United States Patent
Ali et al.

(10) Patent No.: US 7,732,432 B2
(45) Date of Patent: Jun. 8, 2010

(54) 17-CARBAMOYLOXY CORTISOL DERIVATIVES AS SELECTIVE GLUCOCORTICOID RECEPTOR MODULATORS

(75) Inventors: Amjad Ali, Piscataway, NJ (US); James M. Balkovec, Martinsville, NJ (US); Donald W. Graham, Mountainside, NJ (US); Mark L. Greenlee, Plainfield, NJ (US); Gayle E. Taylor, Jersey City, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1342 days.

(21) Appl. No.: 10/540,757

(22) PCT Filed: Jan. 16, 2004

(86) PCT No.: PCT/US2004/001191

§ 371 (c)(1),
(2), (4) Date: Jun. 23, 2005

(87) PCT Pub. No.: WO2004/066920

PCT Pub. Date: Aug. 12, 2004

(65) Prior Publication Data
US 2006/0063746 A1 Mar. 23, 2006

Related U.S. Application Data

(60) Provisional application No. 60/441,629, filed on Jan. 21, 2003.

(51) Int. Cl.
*A61K 31/56* (2006.01)
*C07J 5/00* (2006.01)
(52) U.S. Cl. .................. 514/178; 514/179; 552/570
(58) Field of Classification Search .............. 552/570; 514/178, 179
See application file for complete search history.

(56) References Cited

U.S. PATENT DOCUMENTS

| 4,328,221 A | 5/1982 | Szilagyi nee Farago et al. |
| 4,397,782 A | 8/1983 | Varma |

FOREIGN PATENT DOCUMENTS

| EP | 0 496 520 A1 | | 7/1992 |
| WO | WO 98/20151 | * | 5/1998 |
| WO | WO 00/48572 | | 8/2000 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. (Advanced Drug Delivery Reviews, 48 (2001), pp. 3-26).*
Farenholtz, et al. "Steroidal Imidazole-1-carboxylic Acid Esters", Journal of Medicinal Chemistry, 1974, 17(3), p. 337-342.

* cited by examiner

*Primary Examiner*—Barbara P Badio
(74) *Attorney, Agent, or Firm*—Yong Zhao; Valerie J. Camara

(57) ABSTRACT

The present invention encompasses compounds of Formula (I) or pharmaceutically acceptable salts or hydrates thereof, which are useful as selective glucocorticoid receptor ligands for treating a variety of autoimmune and inflammatory diseases or conditions. Pharmaceutical compositions and methods of use are also included.

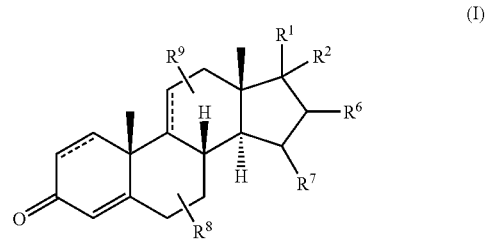

(I)

10 Claims, No Drawings

17-CARBAMOYLOXY CORTISOL DERIVATIVES AS SELECTIVE GLUCOCORTICOID RECEPTOR MODULATORS

CROSS REFERENCE TO RELATED APPLICATIONS

This application is a U.S. national Phase application under 35. U.S.C. §371 of PCT Application No. PCT/US2004/001191, filed Jan. 16, 2004, which claims priority under 35 U.S.C. 119 to U.S. No. 60/441,629, filed 21 Jan. 2003.

BACKGROUND OF THE INVENTION

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and, of these receptors, the glucocorticoid receptor has an essential role in regulating human physiology and immune response. Steroids that interact with the glucocorticoid receptor have been shown to be potent anti-inflammatory agents. The present invention is directed to a novel class of compounds that are selective glucocorticoid receptor modulators that have potent anti-inflammatory and immunosuppressive activity and possess advantages over steroidal glucocorticoid ligands with respect to side effects, efficacy, toxicity and/or metabolism.

SUMMARY OF THE INVENTION

The present invention encompasses compounds of Formula I:

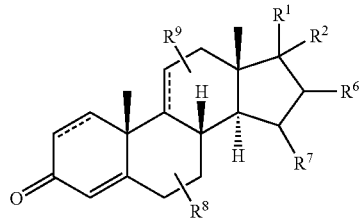

I or pharmaceutically acceptable salts or hydrates thereof, which are useful as selective glucocorticoid receptor ligands for treating a variety of autoimmune and inflammatory diseases or conditions. Pharamaceutical compositions and methods of use are also included.

DETAILED DESCRIPTION OF THE INVENTION

In one aspect, the present invention encompasses compounds of Formula I

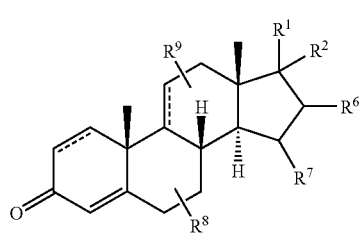

I or a pharmaceutically acceptable salt or hydrate thereof, wherein:

$R^1$ is —C(O)-$R^5$;
$R^2$ is —O—C(O)—N($R^3$)($R^4$), and
or $R^1$ and $R^2$ are joined so that together with the carbon atom to which they are attached is formed a group selected grom the group consisting of

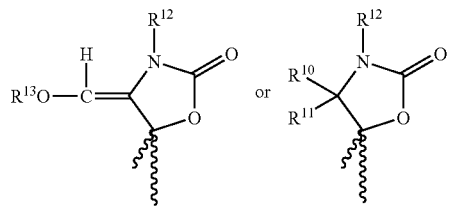

$R^{13}$ is hydrogen or —C(O)—$CH_3$;
$R^3$, $R^6$, $R^7$ and $R^{12}$ are independently in selected from the group consisting of
  (1) hydrogen, and
  (2) $C_{1-3}$alkyl;
$R^4$ is selected from the group consisting of
  (1) $C_{1-10}$alkyl,
  (2) $C_{2-6}$alkenyl,
  (3) aryl, wherein aryl is selected from the group consisting of phenyl and naphthyl,
  (4) heteroaryl, wherein the heteroaryl is selected from the group consisting of pyridyl, furanyl, thienyl and imidazoyl,
  (5) $C_{1-6}$alkyl-aryl, wherein aryl is selected from the group consisting of phenyl and naphthyl,
  (6) —$C_{1-6}$alkyl-heteroaryl, wherein the heteroaryl is selected from the group consisting of pyridyl, furanyl, thienyl and imidazoyl,
    wherein choices (1) and (2) and the alkyl portion of choices (5) and (6) are optionally mono- di- or tri-substituted with substituents independently selected from the group consisting of —OH, —$OCH_3$, —$OCF_3$, —$COCH_3$, —$CO_2CH_3$, —$CONH_2$, —CN, —$SO_2CH_3$, —$SO_2CH_3$, —$SO_2NH_2$, F, Cl, Br, and —$CF_3$ and wherein choices (3) and (4) and the aryl and hereroaryl portion of choices (5) and (6) are optionally mono- or di- substituted with substituents independently selected from the group consisting of —OH, —$OCH_3$, —$OCF_3$, —$COCH_3$, —$CO_2CH_3$, —$CONH_2$, —CN, —$SO_2CH_3$, —$SO_2CH_3$, —$SO_2NH_2$, F, Cl, Br, and —$CF_3$;

or R3 and R4 are joined so that together with the nitrogen atom to which they are attached is formed a ring of 5, 6, 7 or 8 carbon atoms, the ring being optionally substituted with —$C_{1-6}$ alkyl or —$C_{1-6}$alkenyl;
$R^5$ is each independently selected from the group consisting of
  (1) hydrogen,
  (2) $C_{1-6}$alkyl,
  (3) $C_{1-6}$alkyl, substituted with hydroxy,
  (4) $C_{1-6}$alkyl, mono or di-substituted with halo,
  (5) —$C_{1-6}$alkyl-O—C(O)—$C_{1-4}$alkyl,
  (6) —$C_{1-6}$alkyl-O—C(O)—$C_{1-4}$alkyl, optionally mono or di-substituted with halo, hydroxy or methyl;
  (7) —$C_{1-6}$alkyl-S(O)$_n$—$C_{1-4}$alkyl, optionally mono or di-substituted with halo, hydroxy or methyl; and
  (8) $C_{2-6}$alkenyl, wherein n is 0, 1 or 2;
$R^8$ and $R^9$ are each independently selected from the group consisting of
(1) hydrogen,
(2) halo,
(3) hydroxy,
(4) $C_{1-6}$alkyl,
(5) $C_{2-6}$alkenyl, and
(6) phenyl, wherein choices (4), (5) and (6) are optionally mono- or di-substituted with substituents independently selected from —OH, —OCH$_3$, —OCF$_3$, —COCH$_3$, —CO$_2$CH$_3$, —CONH$_2$, —CN, —SO$_2$CH$_3$, —SO$_2$CH$_3$, —SO$_2$NH$_2$, F, Cl, Br, and —CF$_3$, $R^{10}$ is selected from the group consisting of
(1) $C_{1-6}$alkyl,
(2) $C_{1-6}$alkyl, substituted with hydroxy or —OR$^{13}$,
(3) $C_{1-6}$alkyl, mono or di-substituted with halo,
(4) —$C_{1-6}$alkyl-O—C(O)—$C_{1-4}$alkyl,
(5) —$C_{1-6}$alkyl-O—C(O)—$C_{1-4}$alkyl, optionally mono or di-substituted with halo, hydroxy or methyl;
(6) —$C_{1-6}$alkyl-S(O)$_n$—$C_{1-4}$alkyl, optionally mono or di-substituted with halo, hydroxy or methyl;

wherein n is 0, 1 or 2;
$R^{11}$ is selected from the group consisting of
(1) hydrogen,
(2) hydroxy,
(3) $C_{1-6}$alkyl,
(4) $C_{1-6}$alkyl, substituted with hydroxy,
(5) $C_{1-6}$alkyl, mono or di-substituted with halo,
(6) —$C_{1-6}$alkyl-O—C(O)—$C_{1-4}$alkyl,
(7) —$C_{1-6}$alkyl-O—C(O)—$C_{1-4}$alkyl, optionally mono or di-substituted with halo, hydroxy or methyl;
(8) —$C_{1-6}$alkyl-S(O)$_k$—$C_{1-4}$alkyl, optionally mono or di-substituted with halo, hydroxy or methyl;

wherein k is 0, 1 or 2.
Within this aspect, there is a genus wherein $R^6$ is hydrogen or methyl.
Within this aspect, there is another genus wherein $R^3$ is hydrogen.
Within this aspect, there is another genus wherein $R^7$ is hydrogen.
Within this aspect, there is another genus wherein $R^8$ is halo.
Within this aspect, there is another genus wherein $R^9$ is hydroxy.
Within this aspect, there is another genus wherein $R^3$ is hydrogen, $R^6$ is methyl and $R^7$ is hydrogen.
Within this genus, there is a sub-genus of compounds of Formula Ia

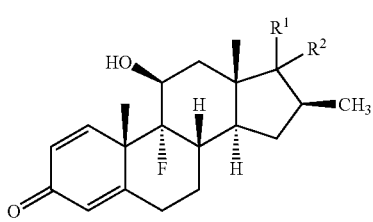

Ia

Another aspect of the invention is the compounds of Formula Ib and pharmaceutically acceptable salts thereof wherein

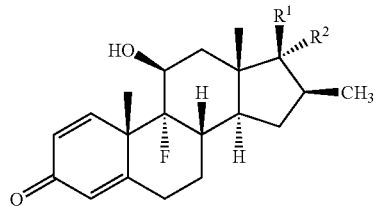

Ib $R^1$ is —C(O)-R$^5$;
$R^2$ is —C(O)—N(H)(R$^4$), and
$R^4$ is selected from the group consisting of
(1) $C_{1-10}$alkyl,
(2) $C_{2-6}$alkenyl,
(3) aryl, wherein aryl is selected from the group consisting of phenyl and naphthyl,
(4) heteroaryl, wherein the heteroaryl is selected from the group consisting of pyridyl, furanyl, thienyl and imidazoyl,
(5) $C_{1-6}$alkyl-aryl, wherein aryl is selected from the group consisting of phenyl and naphthyl,
(6) —$C_{1-6}$alkyl-heteroaryl, wherein the heteroaryl is selected from the group consisting of pyridyl, furanyl, thienyl and imidazoyl, wherein choices (1) and (2) and the alkyl portion of choices (5) and (6) are optionally mono- di- or tri-substituted with substituents independently selected from the group consisting of —OH, —OCH$_3$, —OCF$_3$, —COCH$_3$, —CO$_2$CH$_3$, —CONH$_2$, —CN, —SO$_2$CH$_3$, —SO$_2$CH$_3$, —SO$_2$NH$_2$, F, Cl, Br, and —CF$_3$ and wherein choices (3) and (4) and the aryl and hereroaryl portion of choices (5) and (6) are optionally mono- or di-substituted with substituents independently selected from the group consisting of —OH, —OCH$_3$, —OCF$_3$, —COCH$_3$, —CO$_2$CH$_3$, —CONH$_2$, —CN, —SO$_2$CH$_3$, —SO$_2$CH$_3$, —SO$_2$NH$_2$, F, Cl, Br, and CF$_3$;
$R^5$ is $C_{1-6}$alkyl, substituted with hydroxy or $C_{1-6}$alkyl-O—C(O)—$C_{1-4}$alkyl.

The optional double bonds are as a dotted line and means that the double bond may or may not be present. This is illustrated below for a sub-set of compounds within Formula I:

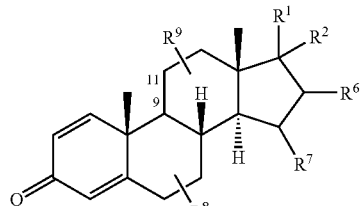

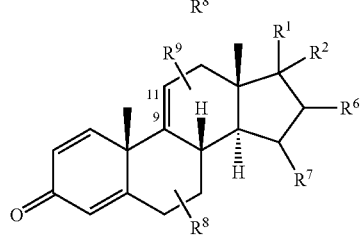

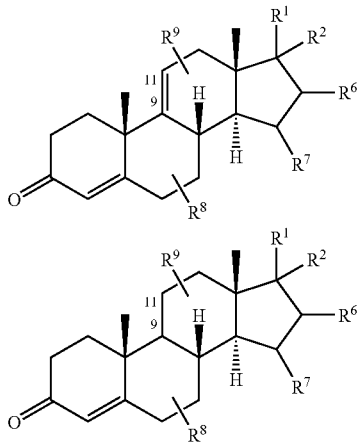

As appreciated by those of skill in the art, $R^8$ can reside on C9 and $R^9$ can reside on C11 only when there is no double bond between C9 and C11.

Illustrating the invention are the following compounds:
(11β,16β)-9-Fluoro-11,21-dihydroxy-16-methyl-3,20-dioxopregna-1,4-dien-17-yl ethylcarbamate,
(11β,16β)-21-(acetyloxy)-9-fluoro-11-hydroxy-16-methyl-3,20-dioxopregna-1,4-dien-17-yl ethylcarbamate,
(11β,16β)-9-fluoro-11,21-dihydroxy-16-methyl-3,20-dioxopregna-1,4-dien-17-yl (1R)-1-phenylethylcarbamate,
(11β,16β)-21-(acetyloxy)-9-fluoro-11-hydroxy-16-methyl-3,20-dioxopregna-1,4-dien-17-yl propylcarbamate,
(11β,16β)-9-fluoro-11,21-dihydroxy-16-methyl-3,20-dioxopregna-1,4-dien-17-yl propylcarbamate,
(11β,16β)-9-fluoro-11,21-dihydroxy-16-methyl-3,20-dioxopregna-1,4-dien-17-yl isopropylcarbamate,
(11β,16β)-9-fluoro-11,21-dihydroxy-16-methyl-3,20-dioxopregna-1,4-dien-17-yl allylcarbamate,
(11β,16β)-21-(acetyloxy)-9-fluoro-11-hydroxy-16-methyl-3,20-dioxopregna-1,4-dien-17-yl butylcarbamate,
(11β,16β)-9-fluoro-11,21-dihydroxy-16-methyl-3,20-dioxopregna-1,4-dien-17-yl butylcarbamate,
(11β,16β)-21-(acetyloxy)-9-fluoro-11-hydroxy-16-methyl-3,20-dioxopregna-1,4-dien-17-yl sec-butylcarbamate,
(11β,16β)-9-fluoro-11,21-dihydroxy-16-methyl-3,20-dioxopregna-1,4-dien-17-yl sec-butylcarbamate,
(11β,16β)-21-(acetyloxy)-9-fluoro-11-hydroxy-16-methyl-3,20-dioxopregna-1,4-dien-17-yl tert-butylcarbamate,
(11β,16β)-9-fluoro-11,21-dihydroxy-16-methyl-3,20-dioxopregna-1,4-dien-17-yl tert-butylcarbamate,
(11β,16β)-21-(acetyloxy)-9-fluoro-11-hydroxy-16-methyl-3,20-dioxopregna-1,4-dien-17-yl pentylcarbamate,
(11β,16β)-9-fluoro-11,21-dihydroxy-16-methyl-3,20-dioxopregna-1,4-dien-17-yl pentylcarbamate,
(11β,16β)-9-fluoro-11,21-dihydroxy-16-methyl-3,20-dioxopregna-1,4-dien-17-yl cyclopentylcarbamate,
(11β,16β)-9-fluoro-11,21-dihydroxy-16-methyl-3,20-dioxo-pregna-1,4-dien-17-yl 1,1,2,2-tetramethyl-propylcarbamate,
(11β,16β)-21-(acetyloxy)-9-fluoro-11-hydroxy-16-methyl-3,20-dioxopregna-1,4-dien-17-yl (1R)-1-phenylethylcarbamate,
(11β,16β)-21-(acetyloxy)-9-fluoro-11-hydroxy-16-methyl-3,20-dioxopregna-1,4-dien-17-yl (1S)-1-phenylethylcarbamate,
(11β,16β)-9-fluoro-11,21-dihydroxy-16-methyl-3,20-dioxopregna-1,4-dien-17-yl (1S)-1-phenylethylcarbamate,
(11β,16β)-9-fluoro-11,21-dihydroxy-16-methyl-3,20-dioxopregna-1,4-dien-17-yl (1S)-1-(methoxycarbonyl)-ethylcarbamate,
(11β,16β)-9-fluoro-11,21-dihydroxy-16-methyl-3,20-dioxopregna-1,4-dien-17-yl phenylcarbamate,
(11β,16β)-9-fluoro-11,21-dihydroxy-16-methyl-3,20-dioxopregna-1,4-dien-17-yl cyclohexylcarbamate,
(11β,16β)-9-fluoro-11,21-dihydroxy-16-methyl-3,20-dioxopregna-1,4-dien-17-yl 1-adamantylcarbamate,
(11β,16β)-9-fluoro-11,21-dihydroxy-16-methyl-3,20-dioxopregna-1,4-dien-17-yl 2-(1-adamantyl)-1,1-dimethylethylcarbamate,
(11β,16β)-9-fluoro-11,21-dihydroxy-16-methyl-3,20-dioxopregna-1,4-dien-17-yl dicyclopropylmethylcarbamate,
(11β,16β)-9-fluoro-11,21-dihydroxy-16-methyl-3,20-dioxopregna-1,4-dien-17-yl spiro[2.4]hept-1-ylmethylcarbamate,
(11β,16β)-9-fluoro-11,21-dihydroxy-16-methyl-3,20-dioxopregna-1,4-dien-17-yl 1,1-dimethylbutylcarbamate,
(11β,16β)-9-fluoro-11,21-dihydroxy-16-methyl-3,20-dioxopregna-1,4-dien-17-yl 1-methylbutylcarbamate,
(11β,16β)-9-fluoro-11,21-dihydroxy-16-methyl-3,20-dioxopregna-1,4-dien-17-yl 1,3-dimethylbutylcarbamate,
(11β,16β)-9-fluoro-11,21-dihydroxy-16-methyl-3,20-dioxopregna-1,4-dien-17-yl isopentylcarbamate,
(11β,16β)-9-fluoro-11,21-dihydroxy-16-methyl-3,20-dioxopregna-1,4-dien-17-yl 3,3-dimethylbutylcarbamate,
(11β,16β)-9-fluoro-11,21-dihydroxy-16-methyl-3,20-dioxopregna-1,4-dien-17-yl tert-pentylcarbamate,
(11β,16β)-9-fluoro-11,21-dihydroxy-16-methyl-3,20-dioxopregna-1,4-dien-17-yl neopentylcarbamate,
(11β,16β)-9-fluoro-11,21-dihydroxy-16-methyl-3,20-dioxopregna-1,4-dien-17-yl 1,2-dimethylpropylcarbamate, and
(11β,16β)-9-fluoro-11,21-dihydroxy-16-methyl-3,20-dioxopregna-1,4-dien-17-yl propylcarbamate.

Another embodiment of the invention encompasses a pharmaceutical composition comprising a compound of Formula I in combination with a pharmaceutically acceptable carrier.

Another embodiment of the invention encompasses a method for treating a glucocorticoid receptor mediated disease or condition in a mammalian patient in need of such treatment comprising administering the patient a compoud of Formula I in an amount that is effective for treating the glucocorticoid receptor mediated disease or condition.

Within this embodiment is encompassed the above method wherein the glucocorticoid receptor mediated disease or condition is selected from the group consisting of: tissue rejection, leukemias, lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity, metabolic syndrome, inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, inflammatory scalp alopecia, panniculitis, psoriasis, discoid lupus erythematosus, inflamed cysts, atopic dermatitis, pyoderma gangrenosum, pemphigus vulgaris, buflous pernphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitus, erythema nodosurn, acne, hirsutism, toxic epidermal necrolysis, erythema multiform, cutaneous T-cell lymphoma, Human Immunodeficiency Virus (HIV), cell apoptosis, cancer, Kaposi's sarcoma, retinitis pigmentosa, cognitive performance, memory and learning enhancement, depression, addiction, mood disorders, chronic fatigue syndrome, schizophrenia, sleep disorders, and anxiety.

Another embodiment of the invention encompasses a method of selectively modulating the activation, repression, agonism and antagonism effects of the glucocorticoid receptor in a mammal comprising administering to the mammal a compound of Formula I in an amount that is effective to modulate the glucocorticoid receptor.

Exemplifying the invention are the compounds of the Examples disclosed hereunder.

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes propenyl, 1-methylethenyl, butenyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the aLkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an araLkyl group as defined above attached to a molecule by an oxygen atom (aralkyl-O) and includes, for example, benzyloxy, and the like.

The term "arylthio" is defined as an aryl group as defined above attached to a molecule by an sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "HET" is defined as a 5- to 10-membered aromatic, partially aromatic or non-aromatic mono- or bicyclic ring, containing 1-4 heteroatoms selected from O, S and N, and optionally substituted with 1-2 oxo groups. Preferably, "HET" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or HET is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

For all of the above definitions, each reference to a group is independent of all other references to the same group when referred to in the Specification. For example, if both $R^1$ and $R^2$ are HET, the definitions of HET are independent of each other and $R^1$ and $R^2$ may be different HET groups, for example furan and thiophene.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The following abbreviations have the indicated meanings:
AIBN=2.2'-azobisisobutyronitrile
B.P.=benzoyl peroxide
Bn=benzyl
$CCl_4$=carbon tetrachloride
D=—$O(CH_2)_3O$—
DAST=diethylamine sulfur trifluoride
DCC=dicyclohexyl carbodiimide
DCI=1-(3-dimethylaminopropyl)-3-ethyl carbodiimide
DEAD=diethyl azodicarboxylate
DIBAL=diisobutyl aluminum hydride
DME=ethylene glycol dimethylether
DMAP=4-(dimethylamino)pyridine
DMF=N,N-dimethylformamide
DMSO=dimethyl sulfoxide
$Et_3N$=triethylamine
LDA=lithium diisopropylamide
m-CPBA=metachloroperbenzoic acid
NBS=N-bromosuccinimide
NSAID=non-steroidal anti-inflammatory drug
PCC=pyridinium chlorochromate
PDC=pyridinium dichromate
Ph=phenyl
1,2-Ph=1,2-benzenediyl
Pyr=pyridinediyl
Qn=7-chloroquinolin-2-yl
$R^s$=—$CH_2SCH_2CH_2Ph$
r.t.=room temperature
rac.=racemic
THF=tetrahydrofuran
THP=tetrahydropyran-2-yl Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamnine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of glucocorticoid receptor mediated diseases the compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

The ability of the compounds of Formula I to selectively modulate glucocorticoid receptors makes them useful for treating, preventing or reversing the progression of a variety of inflammatory and autoimmune diseases and conditions. Thus, the compounds of the present invention are useful to treat, prevent or ameliorate the following diseases or conditions: inflammation, tissue rejection, auto-immunity, various malianancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity and metabolic syndrome.

The compounds of the present invention are also useful for treating, preventing or reversing the progression of disease states involving systemic inflammation such as inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis.

The compounds of the present invention are useful for treating, preventing or reversing the progression of a variety of topical diseases such as inflammatory scalp alopecia, panniculitis, psoriasis, discoid lupus erythematosus, inflamed cysts, atopic dermatitis, pyoderma gangrenosum, pemphigus vulgaris, buflous pernphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma.

The compounds of the present invention are also useful in treating, preventing or reversing the progression of disease states associated with Human Immunodeficiency Virus (HIV), cell apoptosis, and cancer including, but not limited to, Kaposi's sarcoma, immune system activation and modulation, desensitization of inflammatory responses, IIL-I expression, natural killer cell development, lymphocytic leukemia, and treatment of retinitis pigmentosa. Cogitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

The invention also encompasses a method for treating a glucocorticoid receptor mediated disease comprising concomitantly administering to a patient in need of such treatment a compound of Formula I and one or additional more agents. For treating or preventing asthma or chronic obstructive pulmonary disease, the compounds of Formula I may be combined with one or more agents selected from the group consisting of: Θ-agonists (e.g., salmeterol), theophylline, anticholinergics (e.g., atropine and ipratropium bromide), cromolyn, nedocromil and leukotriene modifiers (e.g., montelukast). For treating or preventing inflammation, the compounds of Formula I may be combined with one or the following: a salicylate, including acetylsalicylic acid, a nonsteroidal antiinflammatory drug, including indomethacin, sulindac, mefenamic, meclofenamic, tolfenamic, tolmetin, ketorolac, dicofenac, ibuprofen, naproxen, fenoprofen, ketoprofen, flurbiprofin and oxaprozin, a TNF inhibitor, including etanercept and infliximab, an IL-1 receptor antagonist, a cytotoxic or immunosuppressive drug, including methotrexate, leflunomide, azathioprine and cyclosporine, a gold compound, hydroxychloroquine or sulfasalazine, penicillamine, darbufelone, and a ρ38 kinase inhibitor. The compound of Formula I may also be used in combination with bisphonates such as alendronate to treat a glucocorticoid mediated disease and simultaneously inhibit osteoclast-mediated bone resorption.

The invention will now be illustrated by the following non-limiting examples in which, unless stated otherwise:

(i) all operations were carried out at room or ambient temperature, that is, at a temperature in the range 18-25° C., (ii) evaporation of solvent was carried out using a rotary evaporator under reduced pressure (600-4000 pascals: 4.5-30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 500 MHz or 600 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (litre (s)), mL (millilitres), g (gram(s)), mg (milligrams(s)), mol (moles), mmol (millimoles), eq (equivalent(s)).

EXAMPLE 1

Synthesis of (11β,16β)-9-fluoro-11,21-dihydroxy-16-methyl-3,20-dioxopregna-1, 4-dien-17-yl ethelcarbamate

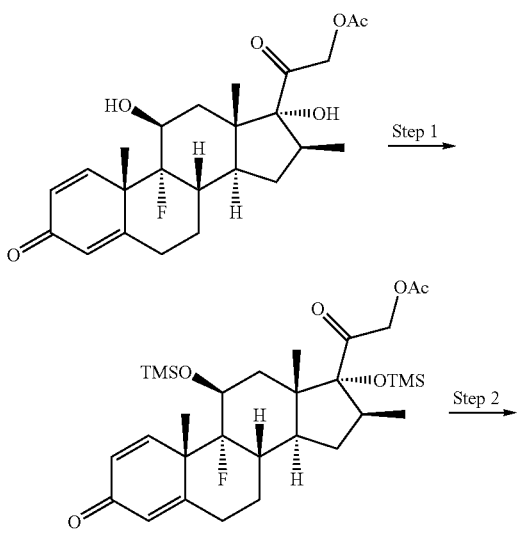

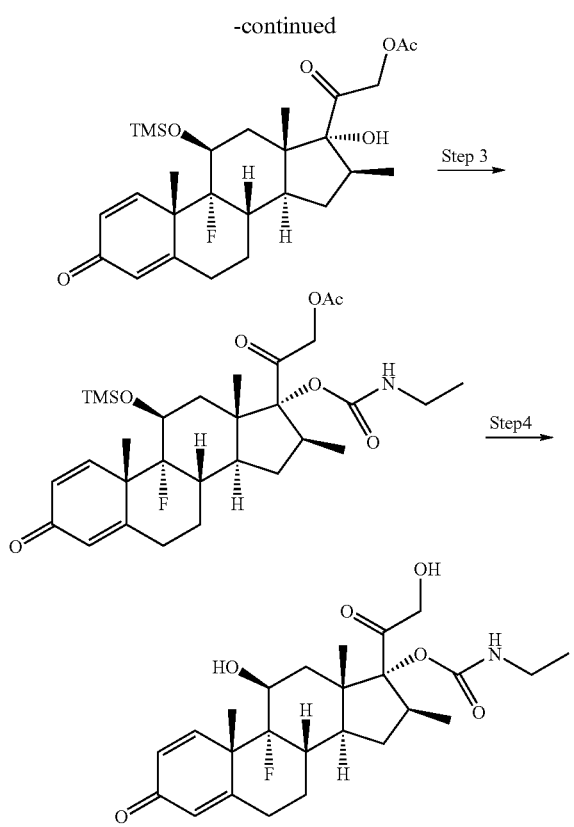

Step 1: (11β,16β)-9-fluoro-16-methyl-3,20-dioxo-11,17-bis[(trimethylsilyl)oxy]pregna-1,4-dien-21-yl acetate To a solution of (11β,16β)-9-fluoro-11,17-dihydroxy-16-methyl-3,20-dioxopregna-1,4-dien-21-yl acetate (18.79 g, 43.25 mmol) and imidazole (58.89 g, 864.9 mmol) in 200 mL of dry N,N-dimethylformamide was added neat trimethylsilyl chloride (55.0 mL, 433 mmol) dropwise during 15 min. The resulting pale yellow solution was stirred at room temperature for 16 hours. The solution was diluted with ethyl acetate and washed successively with water, sat. NH₄Cl, water, sat. NaHCO₃, water, and brine. The organic phase was dried over Na₂SO₄, filtered and evaporated in vacuo to yield 26 g of the title compound as a pale yellow oil.

$^1$H-NMR (500 Mz, CDCl₃): δ0.25 (s, 9H), 0.26 (s, 9H), 0.94 (s, 3H), 1.15-1.25 (m, 1H), 1.21 (d, J=7.3 Hz, 3H), 1.49 (s, 3H), 1.50-1.65 (m, 1H), 1.61 (d, J=13.7 Hz, 1H), 1.85-2.0 (m, 3H), 2.18 (s, 3H), 2.15-2.25 (m, 1H), 2.25-2.50 (m, 3H), 2.55-2.65 (m, 1H), 4.35-4.40 (m, 1H), 4.75 (d, J=17.5 Hz, 1H), 4.84 (d, J=17.5 Hz, 1H), 6.13 (s, 1H), 6.36 (dd, J=10.1, 1.8 Hz, 1H), 7.06 (d, J=10.1 Hz, 1H). MS (ESI): m/z=579.3 (MH⁺).

Step 2: (11β,16β)-9-fluoro-17-hydroxy-16-methyl-3,20-dioxo-11-[(trimethylsilyl)oxy]-pregna-1,4-dien-21-yl acetate A solution of (11β,16β)-9-fluoro-16-methyl-3,20-dioxo-11,17-bis[(trimethylsilyl)oxy]pregna-1,4-dien-21-yl acetate (26 g, ~43 mmol) in 430 mL of tetrahydrofuran (THF) was cooled to 0° C. and neat acetic acid (4.95 mL, 86.5 mmol) was added followed by dropwise addition of a 1.0 M solution of tetra-n-butylammonium fluoride in THF (43.3 mL, 43.3 mmol). After stirring at 0° C. for 4 hours, the ice bath was removed and the reaction was allowed to warm to room temperature and stir for an additional 16 hours. Most of the THF was removed by rotary evaporation in vacuo and the residue was partitioned between ethyl acetate and water. The organic layer was washed successively with water, sat. NH₄Cl, water, sat. NaHCO₃, water and brine. The organic layer was dried over Na₂SO₄, filtered and evaporated under vacuum to give an off-white solid. Purification by flash chromatography through a 1.6 kg column of silica gel eluting with 4% MeOH in dichloromethane provided 16.1 g of the title compound as a white solid.

$^1$H-NMR (500 Mz, CDCl₃): δ0.25 (s, 9H), 1.06 (s, 3H), 1.15-1.25 (m, 1H), 1.17 (d, J=7.1 Hz, 3H), 1.49 (s, 3H), 1.45-1.60 (m, 1H), 1.64 (d, J=14 Hz, 1H), 1.85-2.2 (m, 5H), 2.18 (s, 3H), 2.35-2.55 (m, 3H), 2.55-2.65 (m, 1H), 4.35-4.40 (m, 1H), 4.94 (AB, 2H), 6.11 (s, 1H), 6.35 (dd, J=10.3, 1.8 Hz, 1H), 7.05 (d, J=10 Hz, 1H). MS (ESI): m/z=507.2 (MH⁺).

Step 3: (11β,16β)-21-(acetyloxy)-9-fluoro-16-methyl-3,20-dioxo-11-[(trimethylsilyl)-oxy]pregna-1,4-dien-17-yl ethylcarbamate To a mixture of (11β,16β)-9-fluoro-17-hydroxy-16-methyl-3,20-dioxo-11-[(trimethyl-silyl)oxy]-pregna-1,4-dien-21-yl acetate (3.11 g, 6.15 mmol) in 41 mL of toluene was added neat ethyl isocyanate (20.5 mL, 259 mmol) and the mixture was refluxed for 48 hours. The resulting solution was cooled to room temperature and evaporated under vacuum to leave a slightly gummy solid. Flash chromatography through a 1 kg column of silica gel eluting with t-butyl methyl ether/hexane/chloroform (1:1:1) gave 2.22 g of the title compound as a white solid.

$^1$H-NMR (500 Mz, CDCl₃): δ0.26 (s, 9H), 0.94 (s, 3H), 1.1-1.3 (m, 4H), 1.34 (d, J=6.7 Hz, 3H), 1.48 (s, 3H), 1.45-1.60 (m, 1H), 1.78 (d, J=13.5 Hz, 1H), 1.8-2.1 (m, 3H), 2.16 (s, 3H), 2.15-2.55 (m, 4H), 2.55-2.65 (m, 1H), 3.1-3.3 (m, 2H), 4.35-4.45 (m, 1H), 4.54 (d, J=16 Hz, 1H), 4.82 (d, J=16 Hz, 1H), 5.0-5.1 (m, 1H), 6.11 (s, 1H), 6.34 (d, J=10 Hz, 1H), 7.04 (d, J=10 Hz, 1H). MS (ESI): m/z=578.3 (MH⁺).

Step 4: (11β,16β)-9-fluoro-11,21-dihydroxy-16-methyl-3,20-dioxopregna-1,4-dien-17-yl ethylcarbamate Solid (11β,16β)-21-(acetyloxy)-9-fluoro-16-methyl-3,20-dioxo-11-[(trimethylsilyl)oxy]-pregna-1,4-dien-17-yl ethylcarbamate (2.22 g, 3.84 mmol) was dissolved in 128 mL of a pre-mixed solution of methanol/chloroform/6N HCl (10:2:1) and stirred at room temperature. After 16 hours, an additional 2 mL of 6N HCl was added. After 5 hours more, the solution was partitioned between ethyl acetate and water. The organic phase was washed successively with sat. NaHCO₃, water, and brine. The organic layer was dried over Na₂SO₄, filtered and evaporated in vacuo to give a pale yellow oil. Purification by flash chromatography through a column of 500 g of silica gel, eluting with hexane/ethyl acetate/dichloromethane/methanol (3:3:3:1) yielded 0.890 g of (11β,16β)-9-fluoro-11,21-dihydroxy-16-methyl-3,20-dioxopregna-1,4-dien-17-yl ethylcarbamate as a white powder.

$^1$H-NMR (500 Mz, CDCl₃): δ0.96 (s, 3H), 1.15 (t, J=7 Hz, 3H), 1.15-1.30 (m, 1H), 1.41 (d, J =7.3 Hz, 3H), 1.47 (d, J=13.9 Hz, 1H), 1.56 (s, 3H), 1.50-1.65 (m, 1H), 1.9-2.1 (m, 3H), 2.2-2.7 (m, 7H), 3.1-3.3 (m, 2H), 4.03 (d, J=18 Hz, 1H), 4.26 (d, J=18 Hz, 1H), 4.30-4.45 (m, 1H), 5.2-5.3 (m, 1H), 6.14 (s, 1H), 6.34 (dd, J=10, 1.6 Hz, 1H), 7.21 (d, J=10 Hz, 1H). MS (ESI): m/z=464.2 (MH⁺).

EXAMPLE 2

Synthesis of (11β,16β)-21-(acetyloxy)-9-fluoro-11-hydroxy-16-methyl-3,20-dioxopregna-1,4-dien-17-yl ethylcarbamate

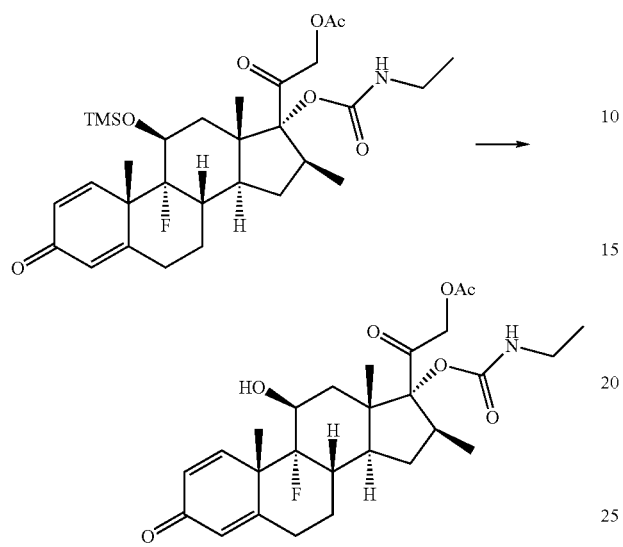

To a solution of (11β,16β)-21-(acetyloxy)-9-fluoro-16-methyl-3,20-dioxo-11-[(trimethylsilyl)-oxy]pregna-1,4-dien-17-yl ethylcarbamate (138 mg, 0.239 mmol) in 2.5 mL of acetonitrile was added boron trifluoride etherate (0.12 mL, 0.96 mmol). After stirring at room temperature for 5 hours, additional boron trifluoride etherate (0.060 mL, 0.47 mmol) was added. The solution was stirred at room temperature for 15 hours more and was then partitioned between ethyl acetate and water. The organic layer was washed with water (twice) and brine and dried over $Na_2SO_4$. Filtration and evaporation under vacuum gave a pale yellow oil. Chromatography on silica gel eluting with hexane/ethyl acetate/dichloromethane/methanol (5:2:2:1) gave (11β,16β)-21-(acetyloxy)-9-fluoro-11-hydroxy-16-methyl-3,20-dioxopregna-1,4-dien-17-yl ethylcarbamate as a white film.

$^1$H-NMR (500 Mz, $CDCl_3$): δ1.01 (s, 3H), 1.18 (t, J=7 Hz, 3H), 1.15-1.30 (m, 1H), 1.37 (d, J =7 Hz, 3H), 1.58 (s, 3H), 1.55-1.65 (m, 1H), 1.8-2.1 (m, 5H), 2.20 (s, 3H), 2.20-2.35 (m, 1H), 2.35-2.55 (m, 3H), 2.6-2.7 (m, 1H), 3.15-3.35 (m, 2H), 4.35-4.50 (m, 1H), 4.54 (d, J=17 Hz, 1H), 4.91 (d, J=17 Hz, 1H), 4.95-5.05 (m, 1H), 6.16 (s, 1H), 6.37 (dd, J=10, 1.6 Hz, 1H), 7.22 (d, J=10 Hz, 1H). MS (ESI): m/z=506.3 ($MH^+$).

EXAMPLE 3

Synthesis of (11β,16β)-9-fluoro-11,21-dihydroxy-16-methyl-3,20-dioxopregna-1,4-dien-17-yl (1R)-1-phenylethylcarbamate

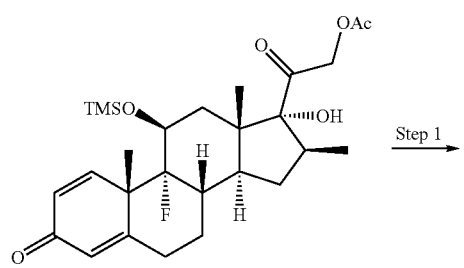

Step 1

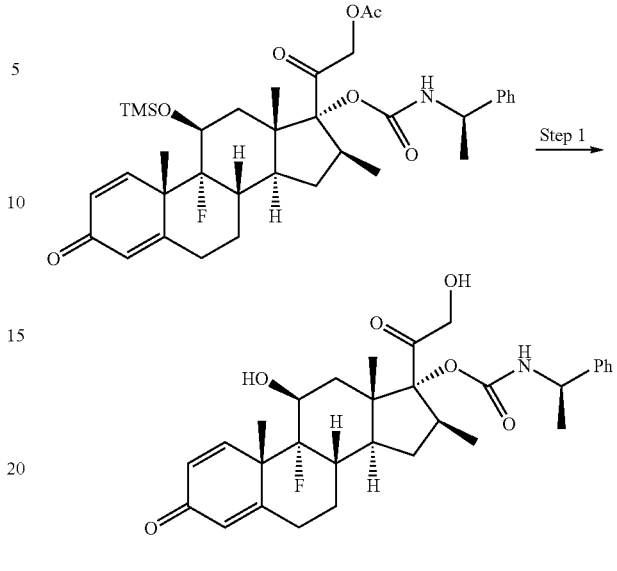

Step 1: (11β,16β)-21-(acetyloxy)-9-fluoro-11-hydroxy-16-methyl 1-3,20-dioxopregna-1,4-dien-17-yl (1R)-1-phenylethylcarbamate To a mixture of (11β,16β)-9-fluoro-17-hydroxy-16-methyl-3,20-dioxo-11-[(trimethyl-silyl)oxy]-pregna-1,4-dien-21-yl acetate (100 mg, 0.197 mmol) and copper (I) chloride (0.5 mg, 0.005 mmol) in 1 mL of N,N-dimethylformamide was added neat (R)-1-phenylethyl isocyanate (0.085 mL, 0.60 mmol). The pale green reaction mixture was stirred at room temperature in the dark for 4.5 hours and was then partitioned between ethyl acetate and water. The organic layer was washed successively with water (twice), sat. $NH_4Cl$, water, and brine and then dried over $Na_2SO_4$. Filtration and evaporation in vacuo gave a foam which was purified by flash chromatography through a 40 g column of silica gel, eluting with hexane/t-butyl methyl ether/chloroform (1:1:1), to provide 67 mg of the title compound as a colorless oil.

MS (ESI): m/z=654.4 ($MH^+$).

Step 2: (11β,16β)-9-fluoro-11,21-dihydroxy-16-methyl-3,20-dioxopregna-1,4-dien-17-yl (1R)-1-phenylethylcarbamate (11β,16β)-21-(acetyloxy)-9-fluoro-11-hydroxy-16-methyl-3,20-dioxopregna-1,4-dien-17-yl (1R)-1-phenylethylcarbamate (42 mg, 0.064 mmol) was dissolved in 1.25 mL of a pre-mixed solution of methanol/chloroform/6N HCl (10:2:1) and stirred at room temperature for 24.5 hours. The solution was then partitioned between ethyl acetate and water and the organic phase was washed with water (twice) and brine and dried over $Na_2SO_4$. Filtration and evaporation under vacuum gave a white film which was purified by preparative thin layer chromatography on silica gel, eluting with ethyl acetate/hexane/dichloromethane/methanol (95:95:95:15), to yield 20 mg of (11β,16β)-9-fluoro-11,21-dihydroxy-16-methyl-3,20-dioxopregna-1,4-dien-17-yl (1R)-1-phenylethylcarbamate as a white solid.

MS (ESI): m/z=540.3 ($MH^+$).

EXAMPLES 4-37

The following compounds were prepared using methods analogous to those described in the preceding examples:

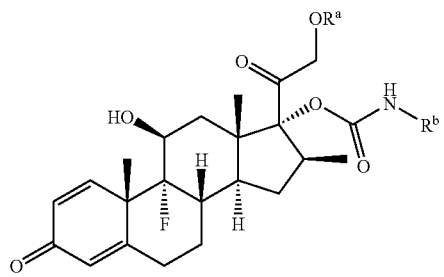

| | | |
|---|---|---|
| 4 | $R^a$ = COCH$_3$<br>$R^b$ = n-Pr | (11β,16β)-21-(aceyloxy)-9-fluoro-11-hydroxy-16-methyl-3,20-dioxopregna-1,4-dien-17-yl propylcarbamate |
| | Mass Spectrum (ESI): m/z = 520.3 (MH$^+$) | |
| 5 | $R^a$ = H<br>$R^b$ = n-Pr | (11β,16β)-9-fluoro-11,21-dihydroxy-16-methyl-3,20-dioxopregna-1,4-dien-17-yl propylcarbamate |
| | Mass Spectrum (ESI): m/z = 478.3 (MH$^+$) | |
| 6 | $R^a$ = H<br>$R^b$ = i-Pr | (11β,16β)-9-fluoro-11,21-dihydroxy-16-methyl-3,20-dioxopregna-1,4-dien-17-yl isopropylcarbamate |
| | Mass Spectrum (ESI): m/z = 478.3 (MH$^+$) | |
| 7 | $R^a$ = H<br>$R^b$ = allyl | (11β,16β)-9-fluoro-11,21-dihydroxy-16-methyl-3,20-dioxopregna-1,4-dien-17-yl allylcarbamte |
| | Mass Spectrum (ESI): m/z = 476.3 (MH$^+$) | |
| 8 | $R^a$ = COCH$_3$<br>$R^b$ = n-Bu | (11β,16β)-21-(acetyloxy)-9-fluoro-11-hydroxy-16-methyl-3,20-dioxopregna-1,4-dien-17-yl butylcarbamate |
| | Mass Spectrum (ESI): m/z = 534.3 (MH$^+$) | |
| 9 | $R^a$ = H<br>$R^b$ = n-Bu | (11β,16β)-9-fluoro-11,21-dihydroxy-16-methyl-3,20-dioxopregna-1,4-dien-17-yl butylcarbamate |
| | Mass Spectrum (ESI): m/z = 492.3 (MH$^+$) | |
| 10 | $R^a$ = COCH$_3$<br>$R^b$ = s-Bu | (11β,16β)-21-(acetyloxy)-9-fluoro-11-hydroxy-16-methyl-3,20-dioxopregna-1,4-dien-17-yl sec-butylcarbamate |
| | Mass Spectrum (ESI): m/z = 534.3 (MH$^+$) | |
| 11 | $R^a$ = H<br>$R^b$ = s-Bu | (11β,16β)-9-fluoro-11,21-dihydroxy-16-methyl-3,20-dioxopregna-1,4-dien-17-yl sec-butylcarbamate |
| | Mass Spectrum (ESI): m/z = 492.4 (MH$^+$) | |
| 12 | $R^a$ = COCH$_3$<br>$R^b$ = t-Bu | (11β,16β)-21-(acetyloxy)-9-fluoro-11-hydroxy-16-methyl-3,20-dioxopregna-1,4-dien-17-yl tert-butylcarbamate |
| | Mass Spectrum (ESI): m/z = 534.4 (MH$^+$) | |
| 13 | $R^a$ = H<br>$R^b$ = t-Bu | (11β,16β)-9-fluoro-11,21-dihydroxy-16-methyl-3,20-dioxopregna-1,4-dien-17-yl tert-butylcarbamate |
| | Mass Spectrum (ESI): m/z = 292.3 (MH$^+$) | |
| 14 | $R^a$ = COCH$_3$<br>$R^b$ = n-pentyl | (11β,16β)-21-(acetyloxy)-9-fluoro-11-hydroxy-16-methyl-3,20-dioxopregna-1,4-dien-17-yl pentylcarbamate |
| | Mass Spectrum (ESI): m/z = 548.3 (MH$^+$) | |
| 15 | $R^a$ = H<br>$R^b$ = n-pentyl | (11β,16β)-9-fluoro-11,21-dihydroxy-16-methyl-3,20-dioxopregna-1,4-dien-17-yl pentylcarbamate |
| | Mass Spectrum (ESI): m/z = 506.3 (MH$^+$) | |
| 16 | $R^a$ = H<br>$R^b$ = cyclopentyl | (11β,16β)-9-fluoro-11,21-dihydroxy-16-methyl-3,20-dioxopregna-1,4-dien-17-yl cyclopentylcarbamate |
| | Mass Spectrum (ESI): m/z = 504.2 (MH$^+$) | |
| 17 | $R^a$ = H<br>$R^b$ = *(1,1,2,2-tetramethylpropyl group)* | (11β,16β)-9-fluoro-11,21-dihydroxy-16-methyl-3,20-dioxo-pregna-1,4-dien-17-yl 1,1,2,2-tetramethyl-propylcarbamate |
| | Mass Spectrum (ESI): m/z = 548.3 (MH$^+$) | |
| 18 | $R^a$ = COCH$_3$<br>$R^b$ = *(1R)-1-phenylethyl group* | (11β,16β)-21-(acetyloxy)-9-fluoro-11-hydroxy-16-methyl-3,20-dioxopregna-1,4-dien-17-yl(1R)-1-phenylethylcarbamate |
| | Mass Spectrum (ESI): m/z = 582.2 (MH$^+$) | |

-continued

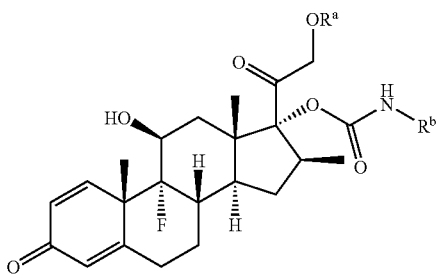

| | | |
|---|---|---|
| 19 | $R^a$ = COCH$_3$ <br> $R^b$ = 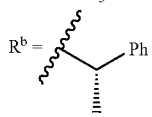 Ph | (11β,16β)-21-(acetyloxy)-9-fluoro-11-hydroxy-16-methyl-3,20-dioxopregna-1,4-dien-17-yl(1S)-1-phenyl-ethylcarbamate |

Mass Spectrum (ESI): m/z = 582.3 (MH$^+$)

| | | |
|---|---|---|
| 20 | $R^a$ = H <br> $R^b$ = 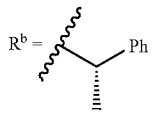 Ph | (11β,16β)-9-fluoro-11,21-dihydroxy-16-methyl-3,20-dioxopregna-1,4-dien-17-yl(1S)-1-phenylethylcarbamate |

Mass Spectrum (ESI): m/z = 540.3 (MH$^+$)

| | | |
|---|---|---|
| 21 | $R^a$ = H <br> $R^b$ = 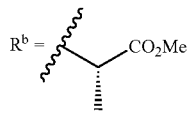 CO$_2$Me | (11β,16β)-9-fluoro-11,21-dihydroxy-16-methyl-3,20-dioxopregna-1,4-dien-17-yl(1S)-1-(methoxycarbonyl)-ethylcarbamate |

Mass Spectrum (ESI): m/z = 522.2 (MH$^+$)

| | | |
|---|---|---|
| 22 | $R^a$ = H <br> $R^b$ = phenyl | (11β,16β)-9-fluoro-11,21-dihydroxy-16-methyl-3,20-dioxopregna-1,4-dien-17-yl phenylcarbamate |

Mass Spectrum (ESI): m/z = 512.2 (MH$^+$)

| | | |
|---|---|---|
| 23 | $R^a$ = H <br> $R^b$ = cyclohexyl | (11β,16β)-9-fluoro-11,21-dihydroxy-16-methyl-3,20-dioxopregna-1,4-dien-17-yl cyclohexylcarbamate |

Mass Spectrum (ESI): m/z = 518.2 (MH$^+$)

| | | |
|---|---|---|
| 24 | $R^a$ = H <br> $R^b$ = 1-adamantyl | (11β,16β)-9-fluoro-11,21-dihydroxy-16-methyl-3,20-dioxopregna-1,4-dien-17-yl 1-adamantylcarbamate |

Mass Spectrum (ESI): m/z = 570.1 (MH$^+$)

| | | |
|---|---|---|
| 25 | $R^a$ = H <br> $R^b$ = 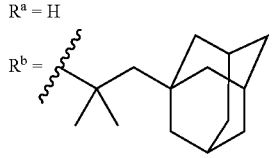 | (11β,16β)-9-fluoro-11,21-dihydroxy-16-methyl-3,20-dioxopregna-1,4-dien-17-yl 2-(1-adamantyl)-1,1-dimethylethylcarbamate |

Mass Spectrum (ESI): m/z = 648.4 (MH$^+$ + Na)

| | | |
|---|---|---|
| 26 | $R^a$ = H <br> $R^b$ = 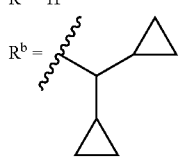 | (11β,16β)-9-fluoro-11,21-dihydroxy-16-methyl-3,20-dioxopregna-1,4-dien-17-yl dicyclopropylmethylcarbamate |

Mass Spectrum (ESI): m/z = 552.3 (MH$^+$ + Na)

| | | |
|---|---|---|
| 27 | $R^a$ = H <br> $R^b$ = 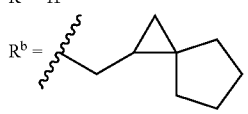 | (11β,16β)-9-fluoro-11,21-dihydroxy-16-methyl-3,20-dioxopregna-1,4-dien-17-yl spiro[2.4]hept-1-yl-methylcarbamate; obtained as a mixture of diastereomers |

Mass Spectrum (ESI): m/z = 566.3 (MH$^+$ + Na)

-continued

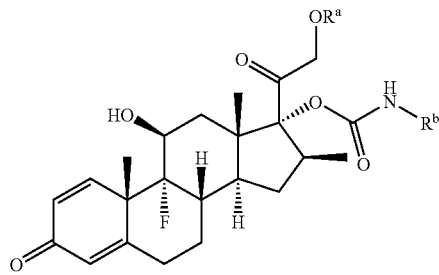

| 28 | $R^a = H$ | (11β,16β)-9-fluoro-11,21-dihydroxy-16-methyl-3,20-dioxopregna-1,4-dien-17-yl 1,1-dimethylbutylcarbamate |

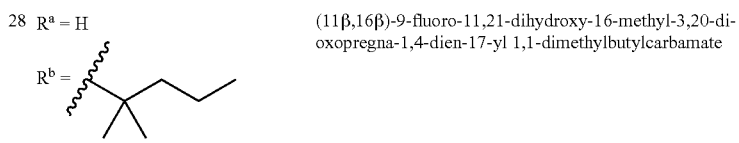

Mass Spectrum (ESI): m/z = 542.3 (MH$^+$ + Na)

| 29 | $R^a = H$ | (11β,16β)-9-fluoro-11,21-dihydroxy-16-methyl-3,20-dioxopregna-1,4-dien-17-yl 1-methylbutylcarbamate; Diastereomer A, first to elute on chiral HPLC |

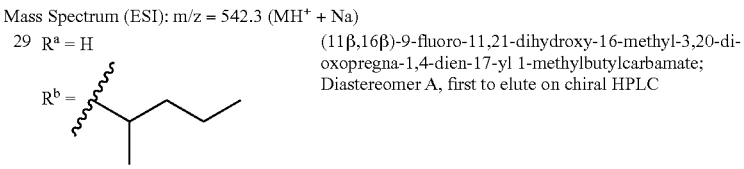

Mass Spectrum (ESI): m/z = 528.3 (MH$^+$ + Na)

| 30 | $R^a = H$ | (11β,16β)-9-fluoro-11,21-dihydroxy-16-methyl-3,20-dioxopregna-1,4-dien-17-yl 1-methylbutylcarbamate; Diastereomer B, second to elute on chiral HPLC |

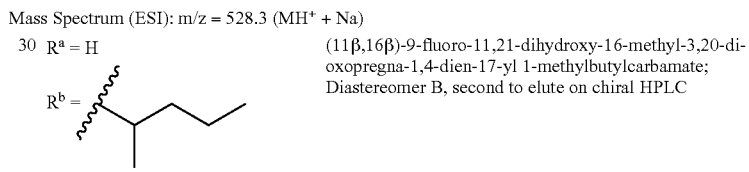

Mass Spectrum (ESI): m/z = 528.3 (MH$^+$ + Na)

| 31 | $R^a = H$ | (11β,16β)-9-fluoro-11,21-dihydroxy-16-methyl-3,20-dioxopregna-1,4-dien-17-yl 1,3-dimethylbutylcarbamate; Diastereomer A, first to elute on chiral HPLC |

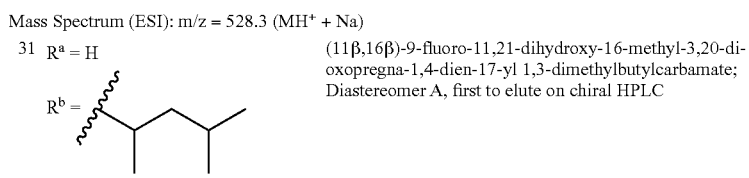

Mass Spectrum (ESI): m/z = 520.3 (MH$^+$)

| 32 | $R^a = H$ | (11β,16β)-9-fluoro-11,21-dihydroxy-16-methyl-3,20-dioxopregna-1,4-dien-17-yl 1,3-dimethylbutylcarbamate; Diastereomer B, second to elute on chiral HPLC |

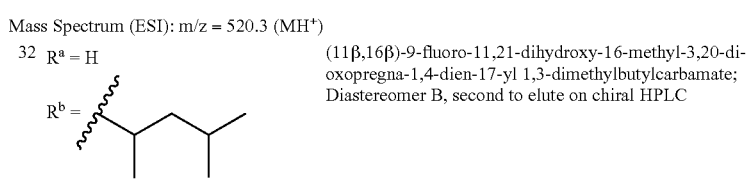

Mass Spectrum (ESI): m/z = 520.3 (MH$^+$)

| 33 | $R^a = H$ | (11β,16β)-9-fluoro-11,21-dihydroxy-16-methyl-3,20-dioxopregna-1,4-dien-17-yl isopentylcarbamate |

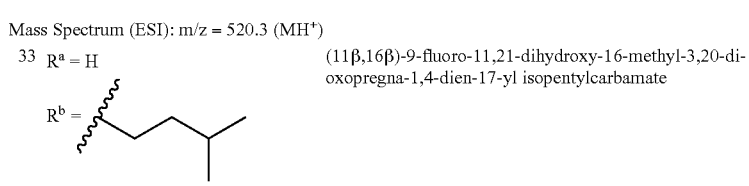

Mass Spectrum (ESI): m/z = 506.3 (MH$^+$)

| 34 | $R^a = H$ | (11β,16β)-9-fluoro-11,21-dihydroxy-16-methyl-3,20-dioxopregna-1,4-dien-17-yl 3,3-dimethylbutylcarbamate |

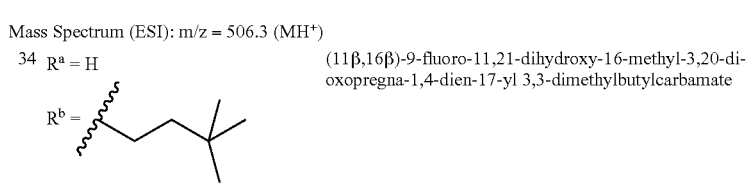

Mass Spectrum (ESI): m/z = 542.1 (MH$^+$ + Na)

-continued

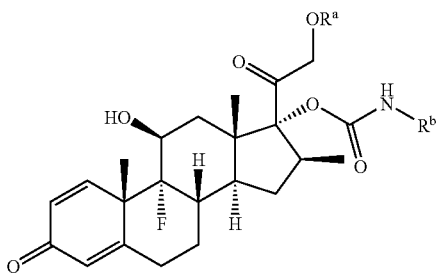

| 35 | $R^a = H$ | (11β,16β)-9-fluoro-11,21-dihydroxy-16-methyl-3,20-dioxopregna-1,4-dien-17-yl tert-pentylcarbamate |

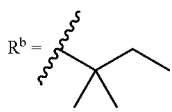

Mass Spectrum (ESI): m/z = 528.2 (MH$^+$ + Na)

| 36 | $R^a = H$ | (11β,16β)-9-fluoro-11,21-dihydroxy-16-methyl-3,20-dioxopregna-1,4-dien-17-yl neopentylcarbamate |

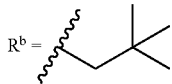

Mass Spectrum (ESI): m/z = 528.1 (MH$^+$ + Na)

| 37 | $R^a = H$ | (11β,16β)-9-fluoro-11,21-dihydroxy-16-methyl-3,20-dioxopregna-1,4-dien-17-yl 1,2-dimethylpropylcarbamate; obtained as a mixture of diastereomers |

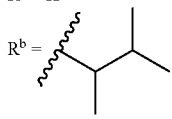

Mass Spectrum (ESI): m/z = 528.4 (MH$^+$ + Na)

EXAMPLE 38

Synthesis of "Cyclized" (11β,16β)-9-fluoro-11,21-dihydroxy-16-methyl-3,20-dioxopregna-1,4-dien-17-yl propylcarbamate

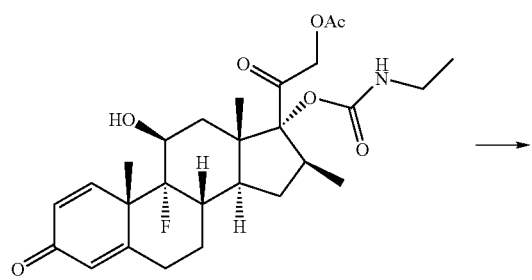

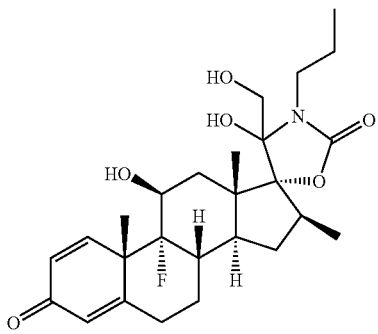

To a solution of (11β,16β)-21-(acetyloxy)-9-fluoro-11-hydroxy-16-methyl-3,20-dioxopregna-1,4-dien-17-yl propylcarbamate (8.5 mg, 0.016 mmol) in 0.3 mL of tetrahydrofuran and 0.1 mL of methanol was added 0.030 mL of a 0.1M solution of potassium carbonate in methanol/water (9:1). After 10 minutes at room temperature, the solution was partitioned between ethyl acetate and water and the organic layer was washed with water (twice) and brine and dried over Na$_2$SO$_4$. The solution was filtered and evaporated in vacuo to give an oil which was purified by preparative thin layer chromatography on silica gel, eluting with ethyl acetate/hexane/dichloromethane/methanol (3:3:3:1), to yield 4.6 mg of the title compound as a semi-solid.

MS (ESI): m/z=478.3 (MH$^+$).

BIOLOGICAL ASSAYS

The activity of the compounds of the present invention as modulators of the glucocorticoid receptor can be evaluated using the following assays:

Ligand Binding Assays

For the hGRI ligand binding assay, cytosols were prepared from recombinant baculovirus expressed receptors. Frozen cell pellets were dounce homogenized in ice cold KPO$_4$ buffer (10 mM KPO$_4$, 20 mM sodium molybdate, 1 mM EDTA, 5 mM DTT and complete protease inhibitor tablets from Boehringer Mannheim) with a "B" plunger. The homogenates were centrifuged at 35,000×g for 1 h at 4° C. in a JA-20 rotor. The IC$_{50s}$ were determined by incubating the cytosols at a final concentration of 2.5 nM [1,2,4,6,7-$^3$H]

Dexamethasone in the presence of increasing concentrations (10-11 to 10-6) of cold dexamethasone or the ligands at 4° C. for 24 h. Bound and free were separated by a gel filtration assay, (Geissler et al, personal communication). Half of the reaction was added to a gel filtration plate (MILLIPORE) containing sephadex G-25 beads that was previously equilibrated with KPO4 buffer containing 1 mg/ml BSA and centrifuiged at 1000×g for 5 min. The reaction plate was centrifuged at 1000×g for 5 min. and the reactions were collected in a second 96-well plate and scintillation cocktail was added and counted in (Wallac) double coincidence beta counter. The $IC_{50s}$ were calculated using a 4-parameter fit program.

The $IC_{50}$ of compounds of Formula I is in the range of 0.1 nM to 1.0 µM. The $IC_{50}$ of compounds of the Examples immediately above is in the range of 1 nM to 400 nM.

What is claimed is:

1. A compound represented by Formula I

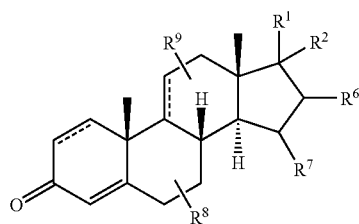

I or a pharmaceutically acceptable salt thereof, wherein:
$R^1$ is —C(O)—$R^5$;
$R^2$ is —O—C(O)—N($R^3$)($R^4$),
$R^3$, $R^6$, and $R^7$ are each independently selected from the group consisting of
(1) hydrogen, and
(2) $C_{1-3}$alkyl;
$R^4$ is selected from the group consisting of
(1) $C_{1-10}$alkyl,
(2) $C_{2-6}$alkenyl,
(3) aryl, wherein aryl is selected from the group consisting of phenyl and naphthyl,
(4) heteroaryl, wherein the heteroaryl is selected from the group consisting of pyridyl, furanyl, thienyl and imidazoyl,
(5) $C_{1-6}$alkyl-aryl, wherein aryl is selected from the group consisting of phenyl and naphthyl,
(6) —$C_{1-6}$alkyl-heteroaryl, wherein the heteroaryl is selected from the group consisting of pyridyl, furanyl, thienyl and imidazoyl,
wherein choices (1) and (2) and the alkyl portion of choices (5) and (6) are optionally mono-di- or tri-substituted with substituents independently selected from the group consisting of —OH, —OCH$_3$, —OCF$_3$, —COCH$_3$, —CO$_2$CH$_3$, —CONH$_2$, —CN, —SO$_2$CH$_3$, —SO$_2$CH$_3$, —SO$_2$NH$_2$, F, Cl, Br, and —CF$_3$ and wherein choices (3) and (4) and the aryl and heteroaryl portion of choices (5) and (6) are optionally mono- or di-substituted with substituents independently selected from the group consisting of —OH, —OCH$_3$, —OCF$_3$, —COCH$_3$, —CO$_2$CH$_3$, —CONH$_2$, —CN, —SO$_2$CH$_3$, —SO$_2$CH$_3$, —SO$_2$NH$_2$, F, Cl, Br, and —CF$_3$;
or R3 and R4 are joined so that together with the nitrogen atom to which they are attached is formed a ring of 5, 6, 7 or 8 carbon atoms, the ring being optionally substituted with —$C_{1-6}$ alkyl or —$C_{1-6}$alkenyl;

$R^5$ is each independently selected from the group consisting of
(1) hydrogen,
(2) $C_{1-6}$alkyl,
(3) $C_{1-6}$alkyl, substituted with hydroxy,
(4) $C_{1-6}$alkyl, mono or di-substituted with halo,
(5) —$C_{1-6}$alkyl-O—C(O)—$C_{1-4}$alkyl,
(6) —$C_{1-6}$alkyl-O—C(O)—$C_{1-4}$alkyl, optionally mono or di-substituted with halo, hydroxy or methyl;
(7) —$C_{1-6}$alkyl-S(O)$_n$—$C_{1-4}$alkyl, optionally mono or di-substituted with halo, hydroxy or methyl; and
(8) $C_{2-6}$alkenyl,
wherein n is 0, 1 or 2;
$R^8$ halo, and
$R^9$ is selected from the group consisting of
(1) hydrogen,
(2) halo,
(3) hydroxy,
(4) $C_{1-6}$alkyl,
(5) $C_{2-6}$alkenyl, and
(6) phenyl,
wherein choices (4), (5) and (6) are optionally mono- or di-substituted with substituents independently selected from —OH, —OCH$_3$, —OCF$_3$, —COCH$_3$, —CO$_2$CH$_3$, —CONH$_2$, —CN, —SO$_2$CH$_3$, —SO$_2$CH$_3$, —SO$_2$NH$_2$, F, Cl, Br, and —CF$_3$.

2. A compound according to claim 1 or a pharmaceutically acceptable salt thereof, wherein:
$R^6$ is hydrogen or methyl.

3. A compound according to claim 1 or a pharmaceutically acceptable salt thereof, wherein:
$R^3$ is hydrogen.

4. A compound according to claim 1 or a pharmaceutically acceptable salt thereof, wherein:
$R^7$ is hydrogen.

5. A compound according to claim 1 or a pharmaceutically acceptable salt thereof, wherein:
$R^9$ is hydroxy.

6. A compound according to claim 1 or a pharmaceutically acceptable salt thereof, wherein:
$R^3$ is hydrogen, $R^6$ is hydrogen or methyl and $R^7$ is hydrogen.

7. A compound according to claim 6 or a pharmaceutically acceptable salt thereof, wherein:

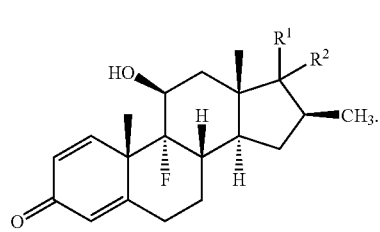

Ia

8. A compound according Formula Ib

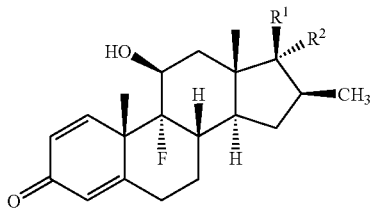

or a pharmaceutically acceptable salt or hydrate thereof, wherein:
$R^1$ is —C(O)—$R^5$;
$R^2$ is —O—C(O)—N(H)($R^4$), and
$R^4$ is selected from the group consisting of
(1) $C_{1-10}$alkyl,
(2) $C_{2-6}$alkenyl,
(3) aryl, wherein aryl is selected from the group consisting of phenyl and naphthyl,
(4) heteroaryl, wherein the heteroaryl is selected from the group consisting of pyridyl, furanyl, thienyl and imidazoyl,
(5) $C_{1-6}$alkyl-aryl, wherein aryl is selected from the group consisting of phenyl and naphthyl,
(6) —$C_{1-6}$alkyl-heteroaryl, wherein the heteroaryl is selected from the group consisting of pyridyl, furanyl, thienyl and imidazoyl,
wherein choices (1) and (2) and the alkyl portion of choices (5) and (6) are optionally mono- di- or tri-substituted with substituents independently selected from the group consisting of —OH, —$OCH_3$, —$OCF_3$, —$COCH_3$, —$CO_2CH_3$, —$CONH_2$, —CN, —$SO_2CH_3$, —$SO_2CH_3$, —$SO_2NH_2$, F, Cl, Br, and —$CF_3$ and wherein choices (3) and (4) and the aryl and heteroaryl portion of choices (5) and (6) are optionally mono- or di-substituted with substituents independently selected from the group consisting of —OH, —$OCH_3$, —$OCF_3$, —$COCH_3$, —$CO_2CH_3$, —$CONH_2$, —CN, —$SO_2CH_3$, —$SO_2CH_3$, —$SO_2NH_2$, F, Cl, Br, and —$CF_3$;
$R^5$ is $C_{1-6}$alkyl, substituted with hydroxy or $C_{1-6}$alkyl-O—C(O)—$C_{1-4}$alkyl.

9. A compound which is
(11β,16β)-9-fluoro-11,21-dihydroxy-16-methyl-3,20-dioxopregna-1,4-dien-17-yl ethylcarbamate,
(11β,16β)-21-(acetylocy)-9-fluoro-11-hydroxy-16-methyl-3,20-dioxopregna-1,4-dien-17-yl ethylcarbamate,
(11β,16β)-9-fluoro-11,21-dihydroxy-16-methyl-3,20-dioxopregna-1,4-dien-17-yl (1R)-1-phenylethylcarbamate,
(11β,16β)-21-(acetyloxy)-9-fluoro-11-hydroxy-16-methyl-3,20-dioxopregna-1,4-dien-17-yl propylcarbamate,
(11β,16β)-9-fluoro-11,21-dihydroxy-16-methyl-3,20-dioxopregna-1,4-dien-17-yl propylcarbamate,
(11β,16β)-9-fluoro-11,21-dihydroxy-16-methyl-3,20-dioxopregna-1,4-dien-17-yl isopropylcarbamate,
(11β,16β)-9-fluoro-11,21-dihydroxy-16-methyl-3,20-dioxopregna-1,4-dien-17-yl allylcarbamate,
(11β,16β)-21-(acetyloxy)-9-fluoro-11-hydroxy-16-methyl-3,20-dioxopregna-1,4-dien-17-yl butylcarbamate,
(11β,16β)-9-fluoro-11,21-dihydroxy-16-methyl-3,20-dioxopregna-1,4-dien-17-yl butylcarbamate,
(11β,16β)-21-(acetyloxy)-9-fluoro-11-hydroxy-16-methyl-3,20-dioxopregna-1,4-dien-17-yl sec-butylcarbamate,
(11β,16β)-9-fluoro-11,21-dihydroxy-16-methyl-3,20-dioxopregna-1,4-dien-17-yl sec-butylcarbamate,
(11β,16β)-21-(acetyloxy)-9-fluoro-11-hydroxy-16-methyl-3,20-dioxopregna-1,4-dien-17-yl tert-butylcarbamate,
(11β,16β)-9-fluoro-11,21-dihydroxy-16-methyl-3,20-dioxopregna-1,4-dien-17-yl tert-butylcarbamate,
(11β,16β)-21-(acetyloxy)-9-fluoro-11-hydroxy-16-methyl-3,20-dioxopregna-1,4-dien-17-yl pentylcarbamate,
(11β,16β)-9-fluoro-11,21-dihydroxy-16-methyl-3,20-dioxopregna-1,4-dien-17-yl pentylcarbamate,
(11β,16β)-9-fluoro-11,21-dihydroxy-16-methyl-3,20-dioxopregna-1,4-dien-17-yl cyclopentylcarbamate,
(11β,16β)-9-fluoro-11,21-dihydroxy-16-methyl-3,20-dioxo-pregna-1,4-dien-17-yl1,1,2,2-tetramethyl-propylcarbamate,
(11β,16β)-21-(acetyloxy)-9-fluoro-11-hydroxy-16-methyl-3,20-dioxopregna-1,4-dien-17-yl (1R)-1-phenylethylcarbamate,
(11β,16β)-21-(acetyloxy)-9-fluoro-11-hydroxy-16-methyl-3,20-dioxopregna-1,4-dien-17-yl(1S)-1-phenylethylcarbamate,
(11β,16β)-9-fluoro-11,21-dihydroxy-16-methyl-3,20-dioxopregna-1,4-dien-17-yl (1S)-1-phenylethylcarbamate,
(11β,16β)-9-fluoro-11,21-dihydroxy-16-methyl-3,20-dioxopregna-1,4-dien-17-yl (1S)-1-(methoxycarbonyl)-ethylcarbamate,
(11β,16β)-9-fluoro-11,21-dihydroxy-16-methyl-3,20-dioxopregna-1,4-dien-17-yl phenylcarbamate,
(11β,16β)-9-fluoro-11,21-dihydroxy-16-methyl-3,20-dioxopregna-1,4-dien-17-yl cyclohexylcarbamate,
(11β,16β)-9-fluoro-11,21-dihydroxy-16-methyl-3,20-dioxopregna-1,4-dien-17-yl1-adamantylcarbamate,
(11β,16β)-9-fluoro-11,21-dihydroxy-16-methyl-3,20-dioxopregna-1,4-dien-17-yl 2-(1-adamantyl)-1,1-dimethylethylcarbamate,
(11β,16β)-9-fluoro-11,21-dihydroxy-16-methyl-3,20-dioxopregna-1,4-dien-17-yl dicyclopropylmethylcarbamate,
(11β,16β)-9-fluoro-11,21-dihydroxy-16-methyl-3,20-dioxopregna-1,4-dien-17-yl spiro[2.4]hept-1-ylmethylcarbamate,
(11β,16β)-9-fluoro-11,21-dihydroxy-16-methyl-3,20-dioxopregna-1,4-dien-17-yl 1,1-dimethylbutylcarbamate,
(11β,16β)-9-fluoro-11,21-dihydroxy-16-methyl-3,20-dioxopregna-1,4-dien-17-yl 1-methylbutylcarbamate,
(11β,16β)-9-fluoro-11,21-dihydroxy-16-methyl-3,20-dioxopregna-1,4-dien-17-yl 1,3-dimethylbutylcarbamate,
(11β,16β)-9-fluoro-11,21-dihydroxy-16-methyl-3,20-dioxopregna-1,4-dien-17-yl isopentylcarbamate,
(11β,16β)-9-fluoro-11,21-dihydroxy-16-methyl-3,20-dioxopregna-1,4-dien-17-yl 3,3-dimethylbutylcarbamate,
(11β,16β)-9-fluoro-11,21-dihydroxy-16-methyl-3,20-dioxopregna-1,4-dien-17-yl tert-pentylcarbamate,
(11β,16β)-9-fluoro-11,21-dihydroxy-16-methyl-3,20-dioxopregna-1,4-dien-17-yl neopentylcarbamate,
(11β,16β)-9-fluoro-11,21-dihydroxy-16-methyl-3,20-dioxopregna-1,4-dien-17-yl1,2-dimethylpropylcarbamate, or
(11β,16β)-9-fluoro-11,21-dihydroxy-16-methyl-3,20-dioxopregna-1,4-dien-17-yl propylcarbamate or a pharmaceutically acceptable salt thereof.

10. A pharmaceutical composition comprising a compound according to claim 1 in combination with a pharmaceutically acceptable carrier.

* * * * *